United States Patent [19]
Lukase et al.

[11] Patent Number: 5,197,878
[45] Date of Patent: Mar. 30, 1993

[54] CLAMP FOR REMOVING A DENTAL PROSTHETIC

[75] Inventors: Stephen P. Lukase, Glendale, Ariz.; Thomas A. Lukase, 2670 Greentree La., La Jolla, Calif. 92037

[73] Assignee: Thomas A. Lukase, Glendale, Ariz.

[21] Appl. No.: 787,590

[22] Filed: Nov. 4, 1991

Related U.S. Application Data

[63] Continuation of Ser. No. 603,879, Oct. 23, 1990, abandoned.

[51] Int. Cl.⁵ .............................................. A61C 3/00
[52] U.S. Cl. .................................... 433/158; 433/153
[58] Field of Search ............... 433/153, 157, 158, 159, 433/160, 161, 162

[56] References Cited

U.S. PATENT DOCUMENTS

| | | | |
|---|---|---|---|
| 1,756,245 | 4/1930 | Flagstad et al. | 433/158 |
| 2,252,798 | 8/1941 | Arnold | 433/158 |
| 3,690,007 | 9/1972 | Curtis | 433/158 |

FOREIGN PATENT DOCUMENTS

| | | | |
|---|---|---|---|
| 100647 | 4/1937 | Australia | 433/158 |
| 372861 | 4/1923 | Fed. Rep. of Germany | 433/157 |
| 331551 | 11/1935 | Italy | 433/158 |

*Primary Examiner*—Cary E. O'Connor
*Attorney, Agent, or Firm*—Cahill, Sutton & Thomas

[57] ABSTRACT

A two prong clamp is adjustably attachable to a dental prosthetic device with compressible resilient inserts to securely grip and retain the dental prosthetic device without causing damage while a force is applied to the clamp sufficient to dislodge and remove the dental prosthetic device. A tool for engaging and exerting a force upon the clamp or upon a bridge is also shown.

24 Claims, 2 Drawing Sheets

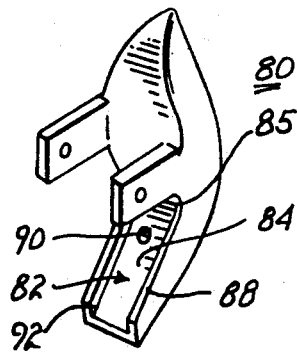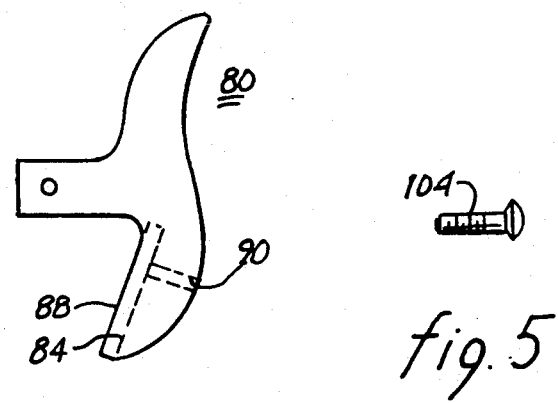
fig. 3  fig. 3a  fig. 5
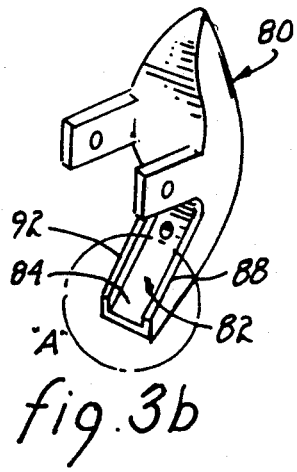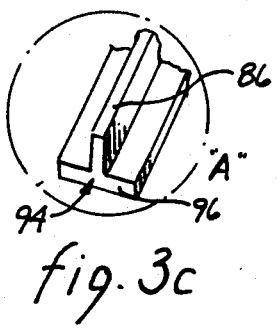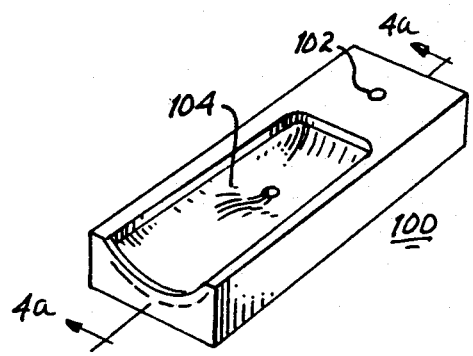
fig. 3b  fig. 3c  fig. 4
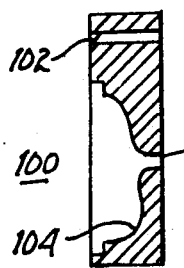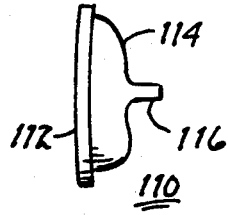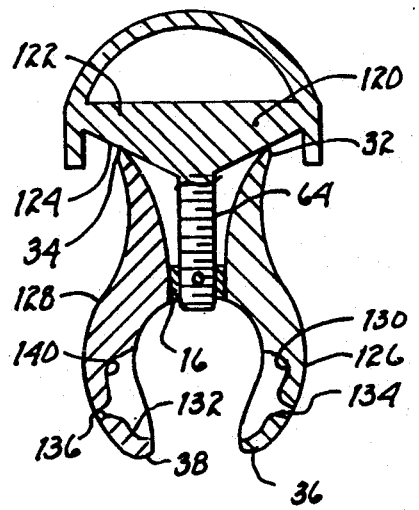
fig. 4a  fig. 4b
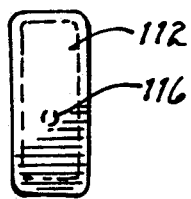
fig. 4c  fig. 6

CLAMP FOR REMOVING A DENTAL PROSTHETIC

CROSS REFERENCE TO RELATED APPLICATION

This is a continuation of copending application Ser. No. 07/603,879, filed Oct. 23, 1990, now abandoned, entitled "CLAMP FOR REMOVING A DENTAL PROSTHETIC".

BACKGROUND OF THE INVENTION

1. Field of the Invention

The present invention relates to dental implements and, more particularly, to gripping elements for removing dental prosthetic devices.

2. Description of the Prior Art

Dental forceps, particularly configured for use upon the anterior, premolar or molar teeth have been available for years for purposes of extracting a tooth. These forceps have jaws particularly angled and of a length to facilitate grasping a particular tooth. During tooth extraction, it is very important that a firm grip of the tooth be achieved and it is of no consequence if the enamel of the tooth cracks or if the tooth is otherwise damaged.

The forceps used for extracting teeth have been developed over a period of many decades to provide an effective combination of gripping a tooth and ease of manipulation of the gripped tooth to effect the extraction process. Primarily, the developmental work has been directed to the length and angulation of the gripping jaws.

To remove a crown for purposes of reattaching it more securely to develop a better seal or for adjustment purposes, it is very important that the crown not be aesthetically damaged o physically distorted. To use a conventional pair of extraction forceps for this purpose presents a real problem for the following reasons. The jaws of the forceps may damage the surface of the crown even though a good firm grip is established. If the forceps ar only lightly squeezed to avoid damage to the crown, the jaws may slip from the crown and cause injury to the patient or damage to other teeth or restorations. For these reasons, many dentists use their fingers, and particularly their fingernails, to grasp the cervical ridge of the crown to dislodge and extract the crown. Since not all dentists have sufficient power in their fingers for this purpose, crown removal is a problem. Similarly, not all dentists have sufficiently robust fingernails to withstand the forces imposed without bending and causing substantial pain to the dentist. A potential problem of fungal infection also exists.

Various devices have been developed over the years to attempt to solve the above enumerated problems. In the 1920s, a clamp forceps was developed which cooperated with a detachably attached rubber dam to minimize damage to a crown while retaining sufficient gripping and extracting force. Regrettably, this device was difficult and awkward to use as a practical matter. Some time later, a pair of forceps was developed which included a pair of opposed curved surfaces lined with resilient material for gripping a crown. These forceps were very difficult to use for all teeth due to the different requirements of grip and manipulation imposed by the placement of each tooth within the mouth.

A yet further device was developed which is of a plier like configuration having one jaw of the pair of jaws oriented to contact and bear against the proximal edge of the crown while the second jaw was penetrably inserted through a passageway cut in the top of the crown to bear against the underlying tooth. In situations where the underlying tooth is little more than a post, this device is ineffective. Moreover, the requirement for a passageway through the cusp of the crown necessitated repair and reconstruction of the crown prior to remounting.

SUMMARY OF THE INVENTION

A pair of prongs of a clamp are adjusted to grasp, firmly retain and support the lingual and labial/buccal surfaces of a crown or to retain a bridge. Any of various implements can be used to engage the clamp to exert the requisite force to remove the crown, bridge or other prosthetic device. To protect the crown or bridge against surface damage and deformation, compressible resilient inserts are mounted on the prongs. A cable pull can be attached to the clamp to apply the requisite force on the clamp.

It is therefore a primary object of the present invention to provide apparatus for grasping and removing without damage a dental prosthetic device.

Another object of the present invention is t provide extraction tools for extracting a dental prosthetic device.

Still another object of the present invention is to provide resilient conformable inserts for a pair of prongs of a clamp to grasp and remove a crown.

Yet another object of the present invention is to provide a cable bridge removing tool.

A further object of the present invention is to provide and adjustably set cable loop for extracting a dental bridge.

A still further object of the present invention is to provide a method for extracting a dental prosthetic device without damaging the device during extraction.

A yet further object of the present invention is to provide a method for firmly grasping but not damaging a dental crown to be removed.

A yet further object of the present invention is to provide replaceable jaw cavities for a pair of jaws of a clamp to grasp and remove a crown.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which:

FIG. 3 is a perspective view of a variant of a clamp arm;

FIG. 3a is a side elevational view of the clamp arm shown in FIG. 3;

FIG. 3b is a partial view of the clamp arm to identify within circle A the area for a variation of configuration;

FIG. 3c illustrates within circle A the variation of the clamp arm;

FIG. 4 is a perspective view of a replaceable tip useable with the clamp arm shown in FIG. 3;

FIG. 4a is a cross sectional view of the replaceable tip shown in FIG. 4;

FIGS. 4b and 4c illustrate an insert useable with the replacement tip shown in FIGS. 4 and 4a;

FIG. 5 is a side view of a representative retainer for the replaceable tip;

FIG. 6 is a side view illustrating a variant of the cap shown in FIGS. 1 and 2;

DESCRIPTION OF THE PREFERRED EMBODIMENT

To assist a dentist in extracting teeth, numerous extraction forceps have been developed for groups of teeth which represent similar or related accessibility, direction of extraction and manipulation impediments. These forceps can generally be categorized as being suitable for anterior, premolar or molar teeth. It is to be understood that further gradations also exist.

When a crown is to be removed in the event the seal for the crown has been compromised or the crown needs to be repaired or adjusted, it is important to prevent damage to the crown during the act of removal. Were such damage to occur, reconstruction or replacement of the crown would result in substantial expense which should be avoided. Because of the fragility of crowns, a dentist often must rely upon the strength of his fingers to effect removal since implements for this purpose and which have a low probability of causing damage to the crown do not exist. All dentists do not have sufficient strength in their fingers to effect removal of a crown. Furthermore, the space or volume available within the oral cavity to manually grip a crown may be a limiting factor of the ease with which a crown can be removed by manual manipulation.

Figure 1:
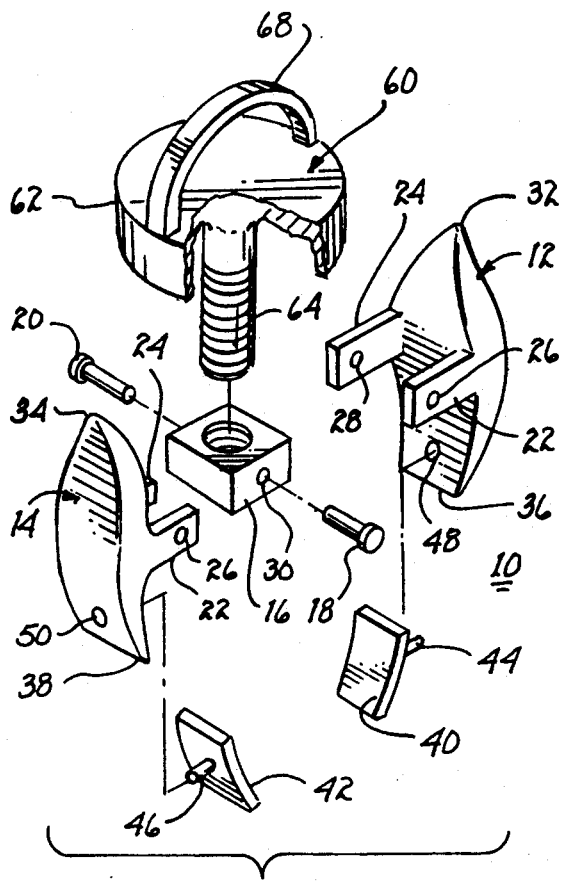
FIG. 1 illustrates in exploded view the component parts of a dental clamp.

Referring to FIG. 1, there is illustrated an exploded isometric view of an adjustable clamp 10 for removing a bridge or a crown. A pair of clamp arms 12,14 are pivotally secured to a nut 16 by pivot pins 18,20. Each of the clamp arms includes a pair of supports 22,24 having apertures 26,28 for penetrably receiving pins 18,20, respectively. The pins may be lodged within bores 30 in nut 16. Necessarily, supports 22,24 of clamp arm 12 must be separated from one another commensurate with the separation between the supports of clamp arm 14 to permit overlap and penetrable engagement by the respective pins. Upper ends 32,34 of each of the clamp arms may be terminated at a point, as illustrated. Lower ends 36,38 are configured to contain cavities that reflect the impression of the labial/buccal and lingual surfaces of the prosthetic to be removed. Further, the lower ends may be channeled to facilitate replacement jaw tips having geometric cavities commensurate with the crown surfaces to be removed.

Since the removal of a crown, as well as a bridge and other dental prosthetic devices, is usually for purposes of repair and/or adjustment, damage to the surfaces and structure should be avoided during extraction. To provide a firm gripping surface and yet protect such crown or dental prosthetic, inserts 40,42 may be employed. These inserts may be made of natural or plastic composition materials to provide a degree of resilience and sufficient friction to firmly grip the crown or dental prosthetic without the imposition of damaging compressive forces. Each insert may be formed to have a generally rectangular surface area, as illustrated. The thickness of each insert is a function of the composition of the material to accommodate ridges and other non smooth curved or planar surfaces of the crown or dental prosthetic. Moreover, to assist in applying uniform forces, the contour of the insert may be configured to conform with the surface of the crown to be extracted.

Inserts 40,42 may include tangs 44,46 extending from the rear surface. These tangs penetrably engage bores 48,50 located in the lower end of clamp arms 12,14, respectively. Similarly, the tangs would also engage the bores of any mounted removable tips. The tangs maintain the inserts positionally fixed. During application of loads, such as during extraction, the compressive forces imposed between each insert and its respective clamp arm will create a substantial amount of friction, which friction will tend to maintain the insert in place during extraction. It is the primary purpose of the tangs to positionally maintain the inserts prior to extraction and during attachment of clamp 10 to the respective tooth.

Figure 2:
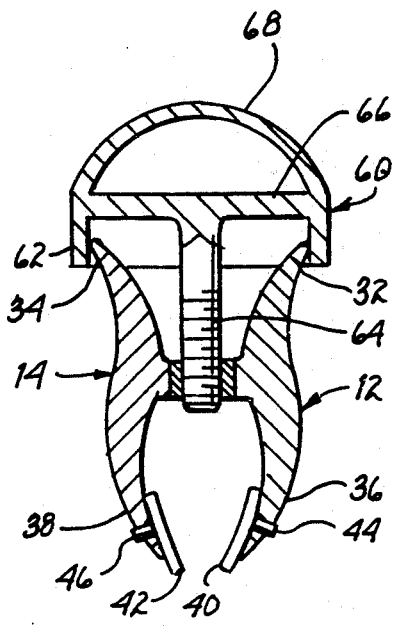
FIG. 2 is a cross sectional view of the dental clamp.
Figure 8:
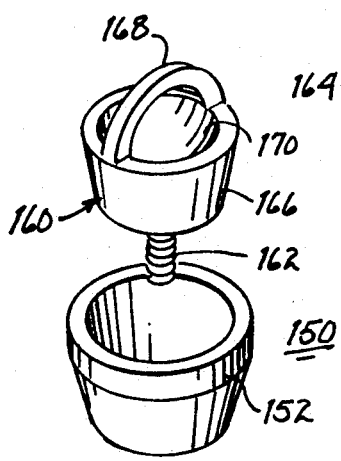
FIG. 8 illustrates cable lock elements.
Figure 9:
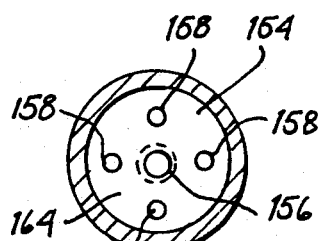
FIG. 9 is a partial cross sectional view taken along lines 9—9, as shown in FIG. 7.
Figure 7:
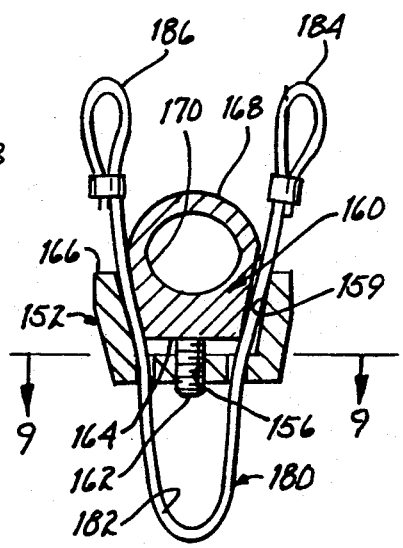
FIG. 7 is a cross sectional view of a cable gripping element usable with the device shown in FIG. 1 or with a bridge.

As particularly illustrated in FIGS. 1 and 2, a cap 60 includes a depending annular shroud 62, which shroud defines the outer limits of a working surface (force enhancing ramp) against which upper ends 32,34 of clamp arms 12,14 operate. A threaded stud 64 depends centrally from base 66 generally concentric with shroud 62, which shroud also depends from the base. The threaded stud is in threaded engagement with nut 16. A loop member 68 extends upwardly from base 66 to assist in rotating the cap relative to the clamp arms and for exerting a lifting force upon the clamp.

To install clamp 10 upon a dental prosthetic device, such as a crown, to be extracted, upper ends 32,34 may be squeezed toward one another to increase the separation between lower ends 36,38 and permit the lower ends to engage opposed sides of the crown. To tighten the lower ends about the opposed sides of the crown, cap 60 is rotated relative to the clamp arms. Such rotation will result in upward movement of nut 16 with commensurate upward movement of upper ends 32,34 of the clamp arms within shroud 62 until the upper ends come in contact with the underside of base 66 (working surface). The lower ends will then be forced toward one another. At this point, the crown will be firmly engaged and somewhat compressed by inserts 40,42 acting against the opposed surfaces of the crown.

By application of an upward force upon loop 68, clamp 10 will lift or extract the crown from the underlying tooth structure. On completion of the extraction procedure, unthreading of cap 60 with respect to the clamp arms will permit release of the crown. It may be noted that upon application of an upward force (or downward force in the case of a crown located in the upper jaw) the force exerted by threaded stud 64 and acting through pins 18,20 upon the clamp arms, may tend to pivot (function of clamp geometry) the lower ends of the clamp arms toward one another and increase the gripping force exerted upon the crown. After extraction, the crown is released from clamp 10 by unscrewing cap 60 completely or at least sufficiently to permit squeezing of upper end 32,34 toward one another to pivot lower ends 36,38 apart from one another.

Except for inserts 40,42, the structure of clamp 10 may be made of a metal alloy or plastic composition to permit autoclaving or other sterilizing techniques. As inserts 40,42 are relatively inexpensive, they may be disposable elements.

Referring jointly to FIGS. 3 and 3a, there is illustrated a variant clamp arm 80 similar to clamp arms 12 and 14 but including a depression or trough 82 for receiving a replaceable tip. The trough may be formed to include a planar bottom surface 84, a rear ridge 85 and two lateral ridges 88,90. The front edge of the bottom surface may be devoid of a ridge, as illustrated. A passageway 92 may extend through the clamp arm in communication with trough 82 to receive means for retaining the replaceable tip within the trough.

For teeth less wide than molars and the like, trough 82 may be too wide to firmly grip the prosthetic device. A variant 94 of the trough configuration illustrated within circle A in FIG. 3b is shown within circle A illustrated in FIG. 3c. The variant includes a base 96, which may be similar to bottom surface 84 of trough 82. A single ridge 86 extends from the base instead of the pair of ridges 88,92 shown in FIG. 3b. An insert (not shown), which may be similar in planform and configuration of the gripping surface for contacting the prosthetic as that used with trough 82, includes a recess for receiving ridge 86. The insert is supported jointly upon the ridge and base 96 extending from the ridge. By employing a single and approximately centered ridge in the clamp arm, the primary gripping force is exerted axially centrally along the prosthetic and the width of the prosthetic has little effect upon the degree of grip. The benefits of a more narrow clamp arm further include an optical advantage in placement of the jaw against the prosthetic device. Moreover, a variety of operative configurations of the insert can be supported adequately upon the combination of ridge 86 and base 96 than is true for the clamp arm trough shown in FIG. 3b.

FIGS. 4 and 4a illustrate a representative replaceable tip 100 for detachable attachment with trough 82. The tip includes a planform commensurate with that of trough 82. A threaded cavity 102 may be incorporated for alignment with passageway 90 in clamp arm 80. A retainer screw, such as machine screw 103 shown in FIG. 5, may be penetrably engaged with passageway 90 and threadedly engaged with threaded cavity 102 to secure the replaceable tip within the trough of the clamp arm. Other substitute means for detachably attaching the replaceable tip may be employed.

Clamp 10 is employed to engage opposed surfaces of the dental prosthetic, such as a crown. To enhance the gripping ability of clamp 100, the opposing replaceable tips are preferably configured to correlate with, if not closely conform with, the contacted labial/buccal or lingual surfaces. Accordingly, replaceable tip 100 includes a depression or socket 104 which is laterally and longitudinally profiled to match the labial/buccal or lingual surface to be contacted. When a pair of clamp arms 80 are employed, each should have attached thereto a replaceable tip corresponding with the surface of the crown (or dental prosthetic) to be extracted. To minimize damage to the crown, an insert 110, and shown in FIGS. 4b, 4c, is attached to each replaceable tip. The insert is preferably of flexible compressible material to permit conformance with the crown or prosthetic surface to be contacted and yet provide sufficient structural robustness to permit application of the requisite forces to effect extraction. The insert includes an exterior surface 112 for contact with the prosthetic device. This surface includes a width and length greater than socket 10 to provide overlap adjacent the edges of the socket and prevent physical contact between the replaceable tip and the prosthetic device. A body portion 114 is configured to be commensurate with and mate with socket 104 of replaceable tip 100. A tang 116 extends from the body portion for penetrable engagement with passageway 106 extending through the replaceable tip from socket 104. By grasping tang 116, insert 110 can be drawn into and seated within socket 104. As the inserts may be of relatively low cost, it is anticipated that they will be disposable and used only one time.

Referring to FIG. 6, there is illustrated a cap 120, which cap is a variant of cap 60. In particular, cap 120 includes a base 122 having a cone shaped under surface 124. This surface extends upwardly and laterally from threaded stud 64. The interaction between upper ends 32,34 and conical surface 124 upon upward movement of nut 16 will enhance the radial outward force exerted upon the upper ends. Thereby, the clamping force afforded by lower ends 36,38 will be augmented.

Clamp arms 126,128 may include a labial cavity 130 and a lingual cavity 140, respectively. Labial cavity 130 also includes a passageway 134 for receiving a tang of an insert (see FIGS. 4b and 4c). Lingual cavity 140 may also include a passageway 136 for receiving the tang of an insert. Thereby, clamp arms 126,128 may be customized to correspond with the dental prosthetic device of a particular tooth.

Referring jointly to FIGS. 7, 8, 9 and 10, there is illustrated a removal tool 150 which is particularly useful in removing dental prosthetic bridges. A cup 152 includes a base 154 having a centrally threaded aperture 156. A plurality of preferably chamfered passageways 158 are disposed in base 154; these passageways may be centered upon an imaginary circle concentric with threaded aperture 156. Cup 152 includes a frusto conical interior wall 159. A slug 160 includes a threaded stud 162 extending from the center of base surface 164 for engaging threaded aperture 156. Slug 160 includes a frusto conical wall 166 having a cone angle equivalent to that of wall 164 for nesting engagement therewith. A loop member 168 extends upwardly from slug 160. The upper surface of slug 160 beneath the loop may include a depression 170 to facilitate engagement of the loop by an implement.

A length of wire or cable 180 extends downwardly through one of apertures 158 and upwardly through another of the apertures to form a loop 182. This loop is placed through or beneath a bridge or other dental prosthetic to be removed. The loop is secured to tool 150 by threadedly engaging slug 160 with cup 152. Upon such threaded engagement, wall 166 will compress the two segments of cable 180 against wall 159. The frictional resistance to movement resulting from such compression will prevent sliding of the cable through tool 150 upon application of a force to either the cable loops or loop 162 of slug 160. To increase the grip of tool 150 upon cable 180, the surfaces of walls 159,166 may be roughened. Preferably, cable 180 is braided steel cable covered with a plastic composition such as that sold under the trademark KYNAR.

Figure 10:
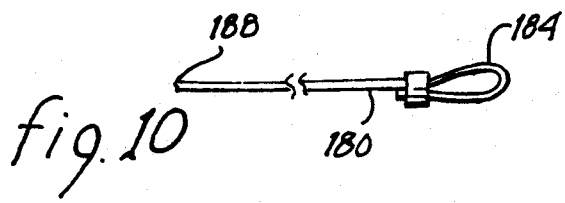
FIG. 10 illustrates a cable with a loop.

Cable 180 may include a loop 184,186 at each end to permit engagement with a slide hammer or other implement. Alternatively, only a single end of cable 180 may include a loop 184, as shown in FIG. 10. The single loop embodiment permits threading of end 188 through apertures 158 to develop loop 182. When cable 180 includes both loops 184,186, passageways 158 must be enlarged sufficiently to accommodate the loops or else the loops must be formed subsequent to engagement of the cable with apertures 158.

It may be noted that more than one cable loop may be employed since, in the embodiment shown, two pairs of passageways 158 are formed in cup 152. Further pairs of passageways may also be formed.

While tool 150 is primarily intended for engaging an exerting a removing force upon a bridge and like dental prosthetic, it may be used with clamp 10. That is, the cable loop can be engaged with loop 68 or other element which is attached to cap 60. Tool 150 will then provide a further, or better, structure for application of a force to remove a crown or other dental prosthetic gripped by clamp 10.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. An extraction tool for removing a dental prosthetic device, said tool comprising in combination:
   a) an opposed pair of clamp arms for gripping opposed sides of the dental prosthetic device, each clamp arm of said pair of clamp arms including an upper end and a lower end;
   b) means for pivotally interconnecting said pair of clamp arms;
   c) means for limiting outward pivotal movement of said upper ends of said pair of clamp arms;
   d) means for urging pivotal movement of said pair of clamp arms and movement of said lower ends toward one another in response to outward limited pivotal movement of said upper ends and away from one another to grip and release, respectively, the dental prosthetic device, said urging means including means for relocating the pivotal interconnection between said pair of clamp arms to urge movement of said lower ends; and
   e) means for accommodating application of a pulling force upon said tool to cause said tool to extract the dental prosthetic device gripped by said pair of clamp arms.

2. The apparatus as set forth in claim 1 including an insert secured to each of said lower ends of said pair of clamp arms for contacting a side of the dental prosthetic device.

3. The apparatus as set forth in claim 2 including means for supporting one of said inserts at each of said lower ends.

4. The apparatus as set forth in claim 3 wherein each of said inserts includes a tang and wherein each of said lower ends includes means for receiving one of said tangs to retain the respective one of said inserts in place.

5. An extraction tool for removing a dental prosthetic device, said tool comprising in combination:
   a) an opposed pair of clamp arms for gripping opposed sides of the dental prosthetic device, each clamp arm of said pair of clamp arms including an upper end and a lower end;
   b) means for pivotally interconnecting said pair of clamp arms intermediate said upper and lower ends, said interconnecting means including at least one apertured support extending from each of said clamp arms and pin means for penetrably engaging each of said apertured supports;
   c) means for limiting the extent of pivotal movement of said upper ends away from one another;
   d) said limiting means including means for translating said interconnecting means relative to said limiting means and as a result of such translation urge pivotal movement of said pair of clamp arms to draw said lower ends toward and away from one another grip and release, respectively, the dental prosthetic device, said translating means including a threaded stud extending from said limiting means and a threaded passageway associated with said pin means for receiving said threaded stud; and
   e) means for accommodating application of a pulling force upon said tool to cause said tool to extract the dental prosthetic device gripped by said lower ends of said pair of clamp arms.

6. The apparatus as set forth in claim 5 wherein said limiting means includes a shroud for limiting separation between said upper ends.

7. The apparatus as set forth in claim 1 wherein each of said lower ends is shovel like.

8. The apparatus as set forth in claim 6 wherein said accommodating means includes a loop.

9. The apparatus as set forth in claim 8 including a base for dependingly supporting said threaded stud and said shroud and for supporting said loop.

10. The apparatus as set forth in claim 6 wherein each of said upper ends includes a point contact or engaging said shroud.

11. The apparatus as set forth in claim 10 wherein each of said lower ends curves in one direction and wherein each of said upper end curves in a different direction.

12. The apparatus as set forth in claim 5 wherein said limiting means includes a force enhancing shroud.

13. An extraction tool for removing a dental prosthetic device, said tool comprising in combination:
   a) an opposed pair of clamp arms for gripping opposed sides of the dental prosthetic device, each clamp arm of said pair of clamp arms including a pair of spaced apart supports;
   b) means for pivotally interconnecting said pair of clamp arms, said interconnecting means including a threaded nut;
   c) pin means for pivotally attaching said pairs of supports to opposed sides of said threaded nut;
   d) means for urging pivotal movement of said pair of clamp arms about said pin means and toward and away from one another to grip and release, respectively, the dental prosthetic device; and
   d) means for accommodating application of a pulling force upon said tool to cause said tool to extract the dental prosthetic device gripped by said pair of clamp arms.

14. A cable lock apparatus for use with a slide hammer to exert an impact force upon a dental prosthetic device to extract the dental prosthetic device, said apparatus comprising in combination:
   a) a cone shaped cup having a base and an interior side wall;
   b) means disposed in said base for penetrably receiving the ends of a cable loop, which cable loop may be engaged with the dental prosthetic device to be extracted;

c) a slug for positionally retaining segments of the cable loop against said interior wall to lock the cable loop in place;
d) means for securing said slug with said cup; and
e) means for connecting the impact hammer with said slug to exert an impact force upon said slug with the impact hammer to extract the cable loop engaged dental prosthetic device.

15. The apparatus as set forth in claim 14 wherein said slug includes a side wall configured to nestingly engage said interior wall.

16. The apparatus as set forth in claim 14 wherein said receiving means comprises apertures for penetrably receiving the segments of the cable loop.

17. The apparatus as set forth in claim 16 wherein said securing means includes threaded means for interconnecting said slug and said cup.

18. The apparatus as set forth in claim 17 wherein said interconnecting means includes a threaded stud extending from said slug and a threaded aperture disposed in said base.

19. The apparatus as set forth in claim 18 wherein said apertures are disposed radially outwardly of said threaded apertures in opposed pairs.

20. The apparatus as set forth in claim 14 wherein said connecting means comprises a loop extending from said slug.

21. The apparatus as set forth in claim 20 wherein said loop extends from opposed sides of said slug.

22. An extraction tool for removing a dental prosthetic device, said tool comprising in combination:
   a) an opposed pair of clamp arms for gripping opposed sides of the dental prosthetic device each clamp arm of said pair of clamp arms including a lower end, a trough disposed in each of said lower ends, a tip mountable within each of said troughs, each of said tips including a cavity having a configuration compatible with the impression contours of the dental prosthetic to be removed, and an insert mountable within each of said cavities for engaging the dental prosthetic to be removed;
   b) means for pivotally interconnecting said pair of clamp arms;
   c) means for urging pivotal movement of said pair of clamp arms toward and away from one another to grip and release, respectively, the dental prosthetic device; and
   d) means for accommodating application of a pulling force upon said tool to cause said tool to extract the dental prosthetic device gripped by said pair of clamp arms.

23. An extraction tool for removing a dental prosthetic device, said tool comprising in combination:
   a) an opposed pair of clamp arms for gripping opposed sides of the dental prosthetic device;
   b) means for pivotally interconnecting said pair of clamp arms;
   c) means for urging pivotal movement of said pair of clamp arms toward and away from one another to grip and release, respectively, the dental prosthetic device;
   d) means for accommodating application of a pulling force upon said tool to cause said tool to extract the dental prosthetic device gripped by said pair of clamp arms;
   e) said urging means including means for translating said interconnecting means relative to said accommodating means which translation brings about pivotal movement of said clamp arms;
   f) said clamp arms including replaceable tips for gripping opposed sides of the dental prosthetic device; and
   g) means for enhancing the gripping force of said clamp arms.

24. An extraction tool for removing a dental prosthetic device, said tool comprising in combination:
   a) an opposed pair of clamp arms for gripping opposed sides of the dental prosthetic device;
   b) means for pivotally interconnecting said pair of clamp arms;
   c) means for urging pivotal movement of said pair of clamp arms toward and away from one another to grip and release, respectively, the dental prosthetic device;
   d) means for accommodating application of a pulling force upon said tool to cause said tool to extract the dental prosthetic device gripped by said pair of clamp arms; and
   e) means for exerting the pulling force upon said tool, said exerting means comprising:
      i) a cone shaped cup having a base and an interior side wall;
      ii) means disposed in said base for penetrably receiving the ends of a cable loop, which cable loop may be engaged with said accommodating means;
      iii) a slug for positionally retaining segments of the cable loop against said interior wall to lock the cable loop in place;
      iv) means for securing said slug with said cup; and
      v) means for connecting an impact hammer with said slug to exert the pulling force upon said slug with the impact hammer.

* * * * *